United States Patent [19]

Eiskamp et al.

[11] Patent Number: 4,750,133
[45] Date of Patent: Jun. 7, 1988

[54] VALIDATION OF KINETIC CHEMICAL REACTION

[75] Inventors: John G. Eiskamp; William M. Blough, both of Fullerton; Robert T. Bell, Mission Viejo, all of Calif.

[73] Assignee: Beckman Instruments, Inc., Fullerton, Calif.

[21] Appl. No.: 516,175

[22] Filed: Jul. 21, 1983

[51] Int. Cl.⁴ .............................................. G01N 31/00
[52] U.S. Cl. ..................................... 364/497; 364/499
[58] Field of Search ............... 364/496, 497, 500, 499, 364/550, 551, 554; 422/67, 68

[56] References Cited

U.S. PATENT DOCUMENTS 4,224,405  9/1980  Hijikata ................................ 364/497
4,236,894  12/1980  Sommervold ........................ 364/497
4,318,615  3/1982  Sagusa et al. ....................... 364/497

Primary Examiner—Errol A. Krass
Attorney, Agent, or Firm—W. H. May; A. Grant; S. R. Markl

[57] ABSTRACT

A method of validating measurement of a kinetic chemical reaction comprises a first tier of validation to validate the ability of a measurement and detection system to provide accurate data, a second tier of validation to validate the initiation and control of the kinetic chemical reaction and a third tier of validation which verifies first that the expected kinetic chemical reaction has proceeded in a characteristic manner and direction, and second, that parameters of the chemical reaction are within limitations characteristic of the measurement and detection system of a measuring instrument investigating the reaction.

2 Claims, 6 Drawing Sheets

VALIDATION OF KINETIC CHEMICAL REACTION

FIELD OF THE INVENTION

This invention relates to the measurement of kinetic chemical reactions, and in particular to the rate of reaction measurement used to determine the activity of an enzyme controlling a reaction.

BACKGROUND OF THE INVENTION

Some chemical substances, such as enzymes, provide catalysis of chemical action without undergoing permanent chemical change. These substances, known as catalysts, remained active only so long as their environment does not cause alteration to their molecular structure. Environmental changes such as pH, increase in temperature, metal ions attaching, and chemical inhibitors reduce catalytic activity of many of these substances. Often the presence of such factors are unpredictable.

For instance, by examining an appropriate enzyme, enzyme activity may be used to estimate a degree of cellular damage to the human body and to suggest a location where such damage may have occurred. Investigations of this type are particularly responsive to determination of cardiac, pancreatic, hepatic, and muscular and bone disorders.

In most kinetic reactions, the rate of conversion of a substrate to a product is a function of the level of the activity of the catalytic substance (enzyme) involved. Activity of this type is generally measured by measuring the absorption or transmittance of light through a solution, which specifically indicates the reduction in concentration of a substrate or the increase in concentration of a product. Transmittance of light can be converted by a logarithmic function to indicate light absorbance. Calculating the logarithm of measured light transmittance provides a linear function indicating absorbance. Absorbance indicates the rate of change in concentration of the substrate or product, which generally is a linear function with time for enzymatic reactions, and thus activity of a catalytic substance (enzyme).

Photometric measurement techniques are important since a common enzyme assay does not correctly measure the concentration of an enzyme in the sample. Rather, the assay monitors the amount of catalytic work or activity performed by the enzyme. To equate this activity measurement to enzyme quantity or concentration, the reaction conditions must be held constant and carefully controlled. Furthermore, these reaction conditions must be established and validated each time the assay is performed.

The study materials of a reaction are referred to as substrates which undergo a chemical change to form products to the reaction. In the presence of catalyzing enzyme, a reaction will proceed to form a product at a rate which depends on the concentration of the enzyme and other factors such as substrate concentration, temperature, and pH. It is important to initially determine that a proper solution mixture has been obtained to allow a reaction to proceed in the proper direction.

The activity of a specific enzyme can be quantitated even in complex mixtures containing other enzymes by measuring what the enzyme can do rather than by measuring the enzyme in terms of its mass or quantity. If substrate or product changes are measured by sensitive procedures, it is possible to relate these changes quantatively to the activity of minute amounts of the associated enzyme. Thus the degree of catalytic activity can be utilized as a precise measurement of enzyme concentration.

Most commonly used is the rate of reaction assay. This method measures the rate at which a substrate is consumed or a product formed with respect to time, rather than the amount of a product or substrate in solution. The maximum rate of change of the substrate or product is directly related to enzyme activity. The maximum rate of conversion of substrate to product, or normally termed the rate of reaction, is easily determined through mathematical means.

The initial rate of an enzymatic reaction is directly proportional to the quantity of active enzyme present when substrate concentrations are at saturated levels and other environmentl variables are optimized and maintained at a constant value.

In some chemical reactions, several possible reaction pathways may exist. Catalysts such as an enzyme may favor one path over another resulting in a different yield of various reaction products, as compared with the uncatalyzed process. This is generally due to reduced energy levels required by a catalyzed process or pathway as compared to the uncatalyzed one. However, such processes often require a base energy level for fulfillment. Thus it may be difficult to ascert along which path a chemical reaction progressed until measurements of selected parameters are performed.

Catalyst (enzyme) activity measurements are accurate only if activity is measured under well defined experimental conditions. Thus the main need for working with enzymes is to define the conditions applicable to each measurement of a specific enzyme or reaction. And once the conditions are defined, a method of validating or assuring these conditions have been maintained is absolutely required.

For instance, a reaction may not proceed as expected due to a number of factors:

(1) concentrations of the reactants may not be as expected;
(2) the age of the solution may be different from expected;
(3) extreme values of pH may have irreversibly denatured the enzyme and thus reducing its ability to catalyze the reaction;
(4) extreme values of temperature may have affected the reaction;
(5) acids or bases may be formed as products from the reaction which may affect the continued process of the reaction.

These numerous factors show a great need for a method to validate the results obtained in measuring a catalyzed (enzymatic) reaction, in view of the number of problems which may cause inaccurate results.

SUMMARY OF THE INVENTION

The present method for validating measurement of a kinetic chemical reaction comprises three groupings of tests, or tiers of validation. A first tier of validation validates the ability of the measurement and detection system to provide accurate data indicating a significant parameter of the chemical reaction being measured. The parameter is generally a rate of conversion formed in the chemical reaction. Validation of the measurement and detection system determines that the devices used for detection and measurement are functioning within expected performance specifications and are thus capable of properly measuring the course of the chemical reaction to give meaningful and useful results reflecting the veritable physical course of the reaction.

A second tier of validation is performed to validate the initiation and control of the kinetic chemical reaction. Validation determines that proper proportions and qualities of sample and reagent have been combined to yield an expected chemical reaction and that control of the variables that govern the reaction are being maintained. Initiated and under control, the chemical reaction will exhibit kinetic activity accurately reflecting the presence of a catalytic substance (enzyme) of interest.

A third tier of this method of validation accomplishes two verfications; one, that the expected kinetic chemical reaction has proceeded in a characteristic manner and direction, and two, that parameters of the chemical reaction which are being investigated (such as rate of reaction), have remained within the limitations characteristic of the measurement and detection system. The tests comprising this third tier of validation discriminate between valid and invalid measurements of an examined parameter by critically evaluating the measurements received. Evaluation is performed through comparison of the linearity and deviation of the measurements with predefined analytical limitations. The analytical limitations are determined from the operating characteristics of the measurement and detection system in measuring clinically precise chemistries and from theoretical predictions of the reaction path which an investigated kinetic chemical reaction should follow.

The first tier of validation comprising the present method may include the following steps to obtain validation of the ability by the measurement and detection system.

1. Validating the output of the system and computing electronics of the measurement system by introduction of known reference inputs and examination of generated outputs responsive to the reference inputs.

2. Validating the information signals responsive to detection of an investigated parameter of a reaction, which are produced by the detection system detecting the chemical reaction. Validation is performed by introduction of a known detectable material and detecting and measuring the material to obtain a response which is compared with known or calculable parameters of the detectable material.

3. Determining system noise effects, e.g., electrical, chemical, physical, etc., which may interfere sufficiently with detection and measurement of a chemical reaction to produce unreliable results.

4. Determining interference of a reaction vessel with the performance of detection operations and the performance of detection systems, which may cause inaccuracy of reaction measurement.

In photometric analysis this step may be accomplished by measurement of the absorbance of light energy by the reaction vessel through which a light beam is directed for measurement of the chemical reaction.

5. Identifying that correct, controlled and sufficient reagent is proportioned into solution with other reactants to generate the kinetic chemical reaction.

The second tier of validation comprising the presented method may include the following steps to assure that a controlled kinetic chemical reaction is initiated:

1. Determining the quality and quantity of reactants which are combined in a reaction vessel for reaction.

In photometric analysis this step may be accomplished by measurement of the initial absorbance of light energy by the reactants singularly or in combination.

2. Determining suitability of the reagent composition for the desired chemical reaction by detection and measurement of the investigated parameter in the reagent, before entry into solution with sample. The results of the measurement may be compared to empirically determined limitations to qualitatively investigate the reagent.

In photometric analysis this step may be accomplished by measurement of the absorbance of light energy by the reagent relative to time and computation of the endogenous rate of reaction generated by the reagent singularly.

3. Indicating introduction of sample into the reaction vessel and quantity and quality of sample, by initial detection and measurement of the investigated parameter exhibited by the reagent and sample solution. Comparison of the results obtained with the results of detection and measurement of the reagent alone in step 2 above, provides an indicator value which may be compared to empirically determined values to test these related sample factors.

In photometric analysis, this may be performed by detecting and measuring initial absorbance of the sample and reagent when mixed in solution at a time during which a commencing reaction is in a lag phase, or shortly after reaction initiation, to determine whether the difference between this measurement and corresponding measurement of the reagent alone indicates suitability of a sample for reaction and measurement. In other words, the adequacy of the quantity and quality of the sample and that the sample has not initially contributed unduly to the measured parameters (absorbance) of the reaction so as to drive the measurement values outside of the accuracy limitations of the measurement system is determined.

The third tier of tests comprising the presented method of validating measurements of a kinetic chemical system includes the following tests to discriminate validity and invalidity of individual and collective data points obtained from measurement of the reaction:

1. Comparing each data point obtained from detection and measurement of the chemical reaction during its occurrence to a predetermined maximum value for such detection and measurement which assures that the performance limitations of the detection and measuring system have not been exceeded. The predetermined value is eimpirically derived from the design performance capabilities of the detection and measuring instrument when measuring clinically accurate samples. For rate of reaction measurements the measured values must remain within the dynamic linear response of the reaction measurement system. This test assures that contaminants or unexpected reactions have not interfered with measurement of the studied parameter in the kinetic reaction.

2. Determining that the activity exhibited by the reaction, obtained through computation of measured data, does not exceed the performance capabilities of the chemical detection and measurement systems. Determination may be made through comparison to empirically determined limitations for reaction rates measured by the instrument of selected chemistry. This test may additionally assure that adjunct reactions between the reagent and sample do not interfere in the analysis of the kinetic reaction being investigated, since interfering adjunct reaction substantially increase reaction rate measurements.

3. Evaluating sets of data obtained from the kinetic reaction to determine; one, that the reaction is proceeding in the correct direction along the desired chemical path; two, that during the measurement time period the activity of the kinetic reaction can be expressed in a linear relationship with respect to time within empirically determined or selected limitations, and three, that the maximum deviation of data obtained is within empirically determined or selected limits from the linear expression.

The second and third sub-tests properly apportion the effect of total system noise in validating measurements of the parameter investigated, to assure that measurable noise is given an increased significance in viewing low magnitude measurement data and decreased significance in reactions which reach large magnitude measurement data values.

DESCRIPTION OF THE BEST MODE

Figure 1:
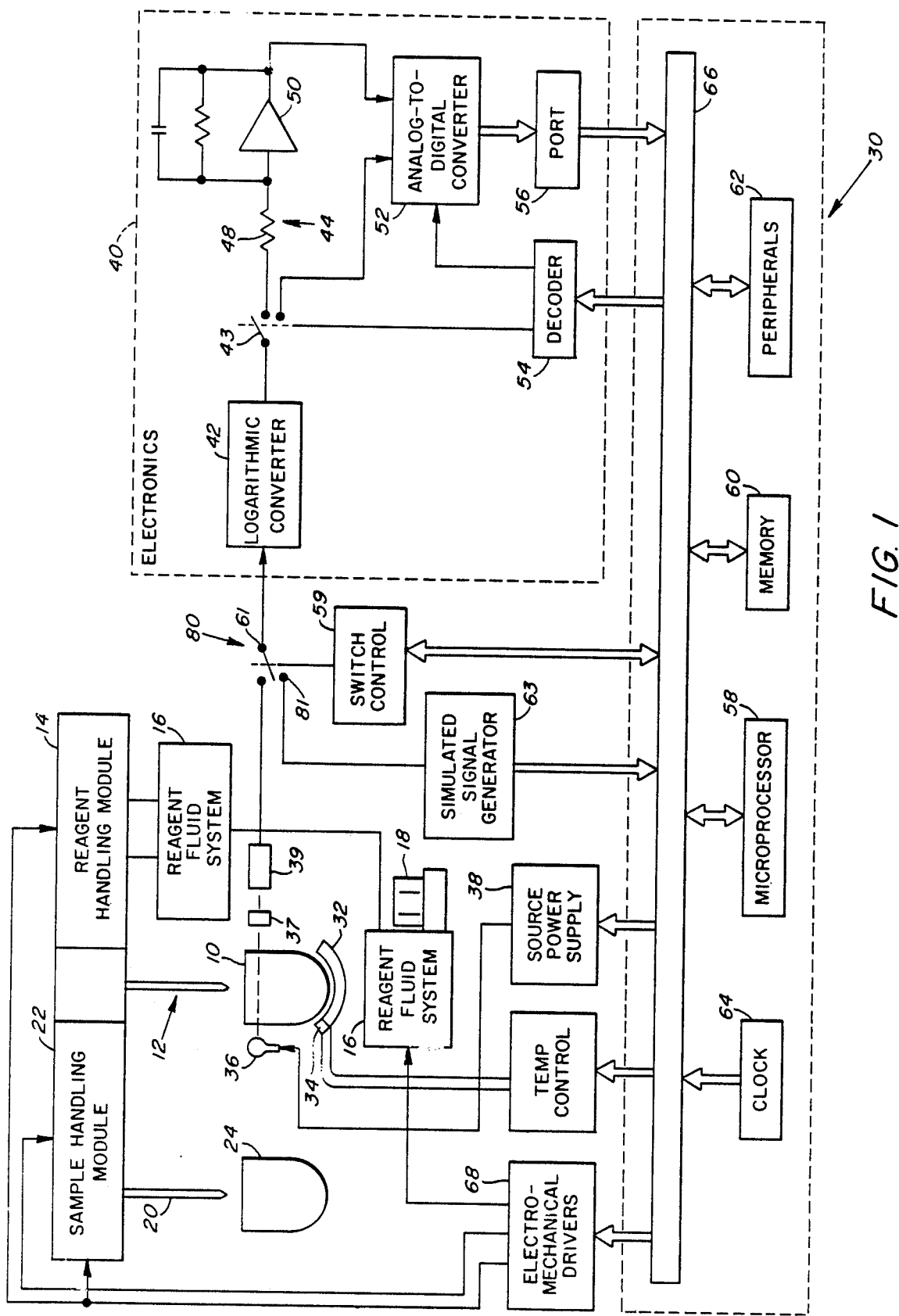
FIG. 1 is a schematic representation of an instrument for assaying kinetic chemical reactions.

An instrument for assaying kinetic chemical reactions is schematically illustrated in FIG. 1. Assay of kinetic reactions generally involves performance of rate reaction measurements which investigate consumption of a substrate or production of a product constituent in the reaction. It is a rate of reaction determination to which the present method of validating measured results is applicable. For example, enzymatic reactions, i.e., chemical reactions catalyzed by an enzyme, are common kinetic chemical reactions in which the rate of change of a constituent or chemical activity, is a parameter of interest. Enzymatic reactions are generally studied by using measurements of specific light energy which is absorbed by a product or a substrate involved in the reaction.

A reaction vessel 10 is provided to hold chemical reagent and sample. The reagent generally contains a substrate to feed a kinetic reaction. Reagent is introduced into the reaction vessel 10 by means of a reagent probe 12 directed by a reagent handling module 14. The reagent handling module 14 moves the reagent probe 12 to and from the reaction vessel 10 to introduce reagent. A reagent fluid system 16 is connected to the reagent handling module 14 to deliver predetermined volumes of reagent through the reagent probe 12 to the reaction vessel 10. The reagent fluid system 16 is connected to fluid conduits which flow measured quantities of reagent from a reagent container 18, through the probe 12 and into the reaction vessel 10. The reagent fluid system may contain, for example, pumps (not shown) driven by stepper motors to provide precise metering of reagent fluids. The total volume of reagent introduced into the reaction vessel is accurately controlled by the pumps to assure a precisely measured volume of reagent is introduced into the reaction.

For many chemical reactions the desired reagent composition is obtained by selectively introducing exact quantities of different reagent components into the reaction vessel. This may be obtained through the use of a plurality of pumps, as described, to obtain an accurately metered reagent composition.

The reaction vessel 10 is preferably constructed of a transparent material having a very low absorbance for light of a wavelength which may be used to perform photometric analysis on a kinetic chemical reaction generated in the vessel 10. Such materials are generally known and include, for example, acrylic, glass or lexan.

Sample is introduced to the reaction vessel 10 by a sample probe 20, directed by a sample handling module 22. The sample handling module 22 moves the sample probe 20 to and from the reaction vessel 10 to introduce sample fluids. A sample container 24 presenting a quantity of sample for analysis is positioned in proximity to the sample handling module 22. The sample handling module 22 directs the sample probe 20 to a first position to enter the sample container 24 and to draw and hold a predetermined volume of sample by operation of precision fluid pumps (not shown). The sample probe 20 is then removed from the sample container 24 and directed to a second position over the reaction vessel 10 into which the sample will be delivered.

The reagent handling module, reagent fluid system, and sample handling module, including the fluid pumps and other elements necessary for operation of the assay instrument, are controlled by a control computer generally indicated as 30. The control computer is programmed by means of selected software programming materials to instruct desired instrument operations and to perform desired data processing functions.

Temperature control of raction vessel 10 is provided by a heat supply means 32 for supplying heat energy to the reaction vessel environment. A temperature sensor means 34 provides an indication of the temperature environment of the reaction vessel 10. The heat supply means 32 is controlled by the control computer 30 in response to signals received from the temperature sensor means 34.

A light source 36 for generating light energy of a selected wavelength needed for analysis is positioned to transmit light through the transparent reaction vessel 10. The light source 36 is connected to a suitable power supply 38 which is controlled by the control computer 30 to supply electrical power to energize the light source when light energy is required for analysis. The light energy transmitted through the reaction vessel 10 is directed through a filter 37 and detected by detector means 39, such as a photodiode or photomultiplier tube. The detector 39 generates an electrical signal proportional to the light energy received. In other words, the detector 39 generates a signal proportional to the light energy transmitted through the reaction vessel and its contents.

The output signal of detector 39 is applied to an electronic circuit 40. The electronic circuit 40 includes a logarithmic converter 42 of conventional design. The output of the logarithmic converter may be applied through a switch 43 directly to an analog-to-digital converter (ADC) 52 or to an amplification circuit 44.

The ADC 52 is controlled via decoder 54 responsive to the control computer 30 to convert a received signal into a binary representation, or code, which is applied through a port 56 to the control computer 30. The decoder 54 may also control the switch 43.

The control computer 30 includes a microprocessor 58, memory 60, peripherals 62, and a real time clock 64, all in communication with a bus 66. The bus 66 is further in communication with the light source power supply 38 the decoder 54 and the port 56. The control computer 30 is of conventional design and may use, for example, a type 8080A microprocessor manufactured by the Intel Corporation or a Z-80 microprocessor as manufactured by Zilog Corporation. Such control computer systems are well known in the art.

The bus 66 is also connected to electromechanical drivers 68 which in turn drive electromechanical components such as peristaltic pumps, stepper motors and electromechanical linear actuators within the sample handling module 22, the reagent handling module 14 and the reagent fluid system 16.

The reagent handling module 14 and sample handling module 22 are controlled by the control computer 30 via electromechanical drivers 68 to draw predetermined volumes of reagent and sample from the sample container into respective probes 12 and 20. The computer 30 then controls the handling modules 14 and 22 to move the probes 12 and 20 sequentially into position above the reaction vessel. The probes 12 and 20 are then directed to inject the contents of predetermined volume into the reaction vessel 10, reagent first followed by sample.

The control computer 30 also controls the switch control 59 which operates switch 61 to alternately connect the input to converter 42 with the detector 39 and a simulated signal generator 63. The signal generator 63 generates electrical signals similar to signals representing analysis of a sample. Simulated signals are applied to the electronics for testing.

At the time of injection, the control computer 30 begins a timing function implemented by the microprocessor 58 and clock 64 in a conventional fashion as by counting down a register or memory address at predetermined time intervals. The timing function is used to time the measurements of the reaction vessel and its contents such that a time value may be determined for each measurement that is made. Preferably, data points are taken at precisely separated periods to provide a uniform interval between measurements.

The measured constituent in the reaction vessel 10 absorbs light within a narrow wavelength band pass range of interference filter 37. In the embodiment disclosed the band pass range is about 340 nanometers. Other light wavelengths may be used depending on the chemical reaction analyzed. As the concentration of the constituent changes, the amount of light energy which reaches the detector 39 changes (i.e., light transmission changes) varying the output of the detector. The logarithmic converter converts the varying output of the detector into a signal which is proportional to the absorbance, and thus the concentration, of the measured constituent in the reaction vessel which is applied to ADC 52 through the electronics 40.

The control computer 30 through the decoder 54 controls ADC 52 to convert the output of the electronic circuit into digital representation. The digital representation is read by the microprocessor through the port 56 and may be stored into the memory 60 in a conventional fashion.

The assay instrument of FIG. 1 is essentially a conventional rate of reaction assay instrument which may be modified in accordance with the teachings presented herein to perform the described method of validating its output. Such modification may comprise, for example, introduction of new or modified software to the memory 60 which, in effect, reconfigures the elements and sequence of operation of the instrument described herein. For example, conventional instruments suitable for modification is an ASTRA Stat/Routine Analyzer manufactured by Beckman Instruments, Inc., including an enzyme chemistry module. Those skilled in the art will recognize that other instruments may exist, be designed or modified in accordance with the teachings herein. Such instruments generally employ sample and reagent handling modules, reagent fluid systems, electronic circuits for performing analog and digital computations, and control techniques well known in the art.

The operation of the analysis apparatus may now be described for performing a rate of reaction analysis of an unknown sample which is mixed in solution with the reagent. Generally, the analysis apparatus performs a kinetic rate analysis for a sample containing an enzyme.

The term reactants as used herein may include a substance involved in the clinical kinetic reaction, whether or not altered. Its use will thus include catalysts such as enzymes.

The operation of the analysis apparatus may proceed by first performing photometric analysis to determine light transmission through the reaction vessel 10 contained in the instrument. Next, an exactly measured amount of reagent may be introduced into the reaction vessel 10. For some chemistries it is necessary to introduce component reactants into the reagent vessel 10 which will be mixed therein to form the reagent as discussed previously. Once the reagent has been introduced into the reaction vessel 10, further photometric tests are performed on the reaction vessel holding reagent to determine light absorbance by the reagent. Next, the sample is introduced into the reaction vessel 10 and mixed with the reagent by a blender (not shown). The reaction between reactants (including enzymes) contained in the sample and the substrate contained in he reagent begins immediately. The reaction progresses through a lag phase during which the reactants (including enzymes) become activated and react with the substrate to form a known product. Once a sufficient number of reactants (including enzymes) are activated the energy generated during the reaction sufficiently activates the remaining reactants in solution to bring the reaction to a maximum rate. The maximum rate is dependent upon the concentration of the enzymes and any environmental factors which affect activity of the reaction. These factors include pH of the solution, temperature, inhibitors to reaction, and associated co-factors, as are commonly known to those experienced in kinetic and enzymatic chemistry reactions.

A measurement of a changing concentration of the substrate consumed or product formed by the reaction relative to time yields an indication of kinetic (enzyme) activity. It is activity that is a measure of the concentration of a catalyst (enzyme) present in the sample, relative to the environmental conditions in which the reaction proceeds. Measurement of changes in concentration of the substrate or product are obtained by photometric techniques which measure transmission of selected wavelength of light through the sample solution (sample and reagent).

Generally, the product formed is selected as the substance to be measured since small amounts of increasing concentration from zero are easily determinable, whereas small decreases from high concentrations in substrate may not be measurable.

As light energy is passed through the reaction vessel holding the sample and reagent, light will be absorbed by the product produced in proportion to its concentration. Thus, depending upon the width of the reaction vessel 10 and thus solution through which the light must traverse, the light transmitted through the solution provides an indication of the concentration of the product.

The relationship between the transmission and absorbance of light is a logarithmic function. By performing a logarithmic calculation on the light transmission value measured by the detector 39, an absorbance value may be obtained. Since increase in absorbance is proportional to the increase in concentration of the light absorbing product, the change in the absorbance value indicates the rate of reaction when compared with the period of time over which the measurements are taken. Theoretically, when the reaction attains its maximum rate, logarithmic calculations of the measured change in light transmission due to absorption of light by the product (which equals change in concentration) with respect to time, is proportional to catalyst (enzyme) activity. Generally, for enzymatic reactions the maximum reaction rate expresses a linear relationship. In other words, the rate of change in product concentration is linear with respect to time. This is known as Beer's Law which is described by the following equation:

$$A = C \times A \times B \times DF \times TC$$

C = Extinction coefficient;
A = Pathlength;
B = Concentration;
DF = Dilution factor; and
TC = Temperature coefficient.

Preferably, ten individual measurements of light transmission are made, separated by intervals of three seconds. The electrical signal obtained from the detector corresponding to each of the measured points contains information of the transmission of the selected wavelength of light through the sample solution. The signal is applied to the electronics 40 to obtain ten individual data points characteristic of the reaction at the time they are taken. Thus, the electrical signal from the detector is applied to the log converter to obtain a linear expression of the rate of reaction, and indicate the activity of the catalyst (enzyme) contained in the sample. This activity is used to indicate the concentration of the catalyst (enzyme) present in the sample which is clinically significant in performing medical diagnosis.

When the kinetic rate analysis is performed, the electronics 40 provide an output value at ten equally spaced periods of time after the reaction begins. These values provide a number of data points which should ideally possess the linear relationship when graphically represented in a plot of time versus activity. The linear relationship as discussed is based upon the logarithmic relationship exhibited between light transmittance and absorbance, which is indicated by the logarithmic data computation performed by the logarithmic converter.

Each of the ten data points is obtained at the end of a time interval equally spaced from adjacent intervals to provide a consistent time dependent analysis of the rate at which the reaction is proceeding. Thus, the data points obtained may be used to accurately indicate the rate of analysis.

The computer controller will direct the electronics 40 to receive a signal from the detector at 10 equally spaced intervals. Each signal received will be a measure of transmittance of light energy having the 360 nm wavelength, through the sample solution. Since transmittance is related to absorbance by the described logarithmic function, the electronics 40 will process each of the signals indicating transmittance to obtain a linear expression of light absorbance versus time. Each of the data points will be converted to indicate an absorbance value. Since each data point was taken (measured) at equally spaced intervals, a graphical illustration of each absorbance value relative to the time value at which the absorbance was measured ideally will yield a linear slope. The slope of these values provides a measure of the rate of the reaction between the sample and reagent governed by the studied catalyst (enzyme). This can be used as a measure of kinetic or enzymatic activity.

The slope may be calculated by simultaneous solution using the generally known formula:

$$y = mx + b$$

where
y equals an absorbance value;
x equals a time value;
m equals the slope; and
b equals the value of y when x equals 0 (constant).

It is generally understood, however, that measured data points will never perfectly meet the ideal linear expression due to a wide range of error introducing factors. Thus, with knowledge that the ideal relationship between changes in absorbance and changes in time should be a linear relationship, a value for the slope may be estimated. This can be illustrated graphically by finding a line of best fit through all of the data points measured. The line of best fit will then yield a slope which is an estimate of the rate of reaction.

A line of best fit may be determined by performing a least squares linear regression of the measured absorbance values using a classical two pass method. The following equation represents the derivation:

$$M = \frac{\Sigma(X_i - \bar{X}_i)(Y_i - \bar{Y}_i)}{\Sigma(X_i - \bar{X}_i)^2}$$

The regression can be performed by methods taught in Method Evaluation, authored by James Westgard, et al., and published by the American Society of Medical Technology in 1978.

Since real measurements will never perfectly fit into the theoretical expression of linearity, a judgment as to correctness of the estimate must be made. In other words, a validation of the data obtained must be performed. This must be done to assure that data received is sufficiently accurate within ranges of expectation, when compared to the ideal theoretical values, to determine that the results obtained are reliable and dependable. Validation is particularly important in kinetic rate of reaction measurement since a great variety of interferences may shorten, change or eliminate the period of time during which the reaction exhibits linear rate characteristics. There are a number of factors which may interfere with accurate measurement of the reaction rate of a kinetic (enzyme) reaction. Thus, a clear need is present for a method of validating measurements obtained to provide a high degree of reliability in the data received, upon which clinical decisions may be based.

The present invention provides a method of validating the data received from a photometric analysis of catalytic (enzymatic) reactions, as described, which yields a high degree of reliability and dependability in measured values which are validated. Moreover, the method is adapted for use with automated clinical analyzers which rapidly perform series of analysis.

Figure 2A:
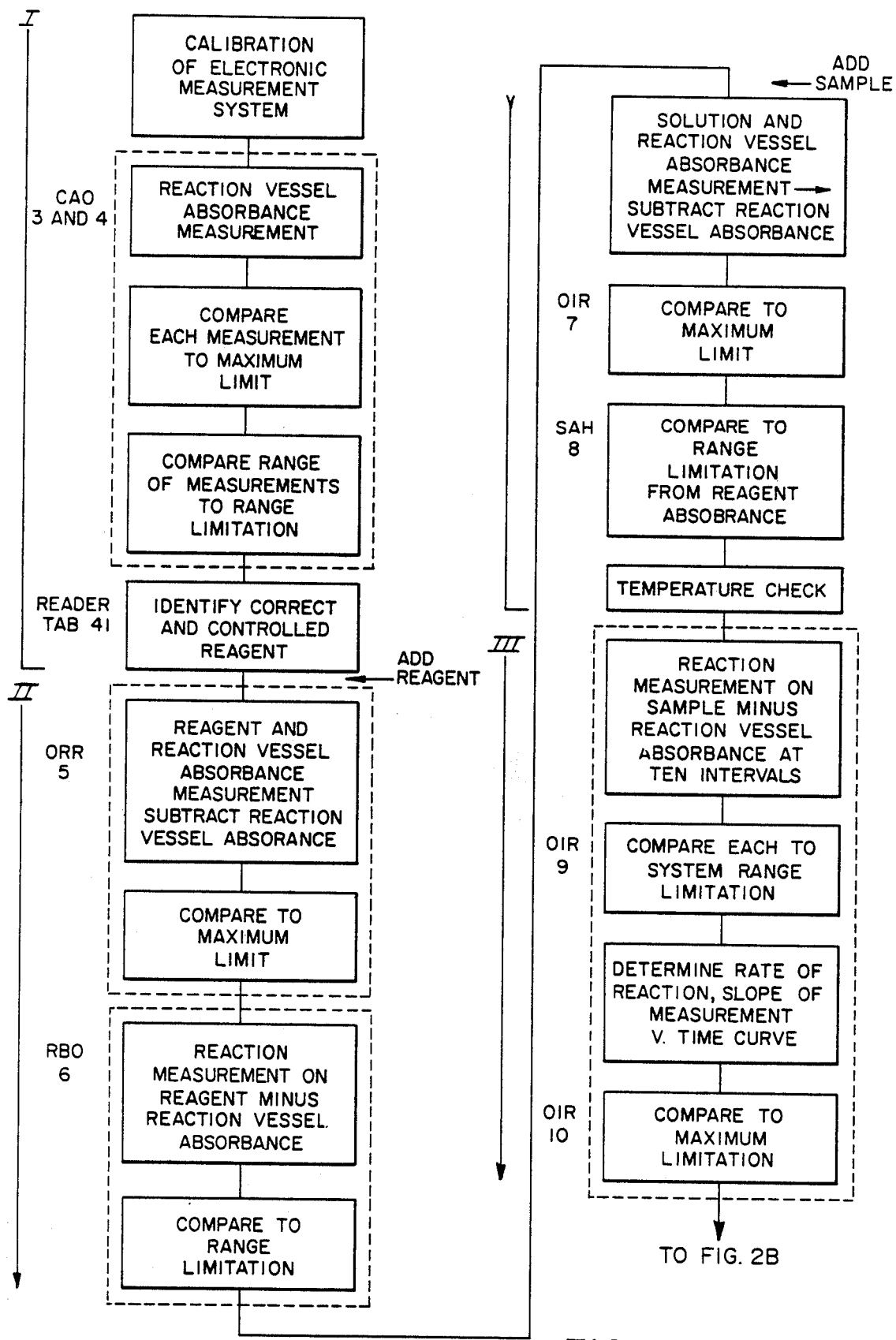
FIG. 2 is a block diagram of the presented method of validating measurement of a kinetic chemical reaction.
Figure 2B:
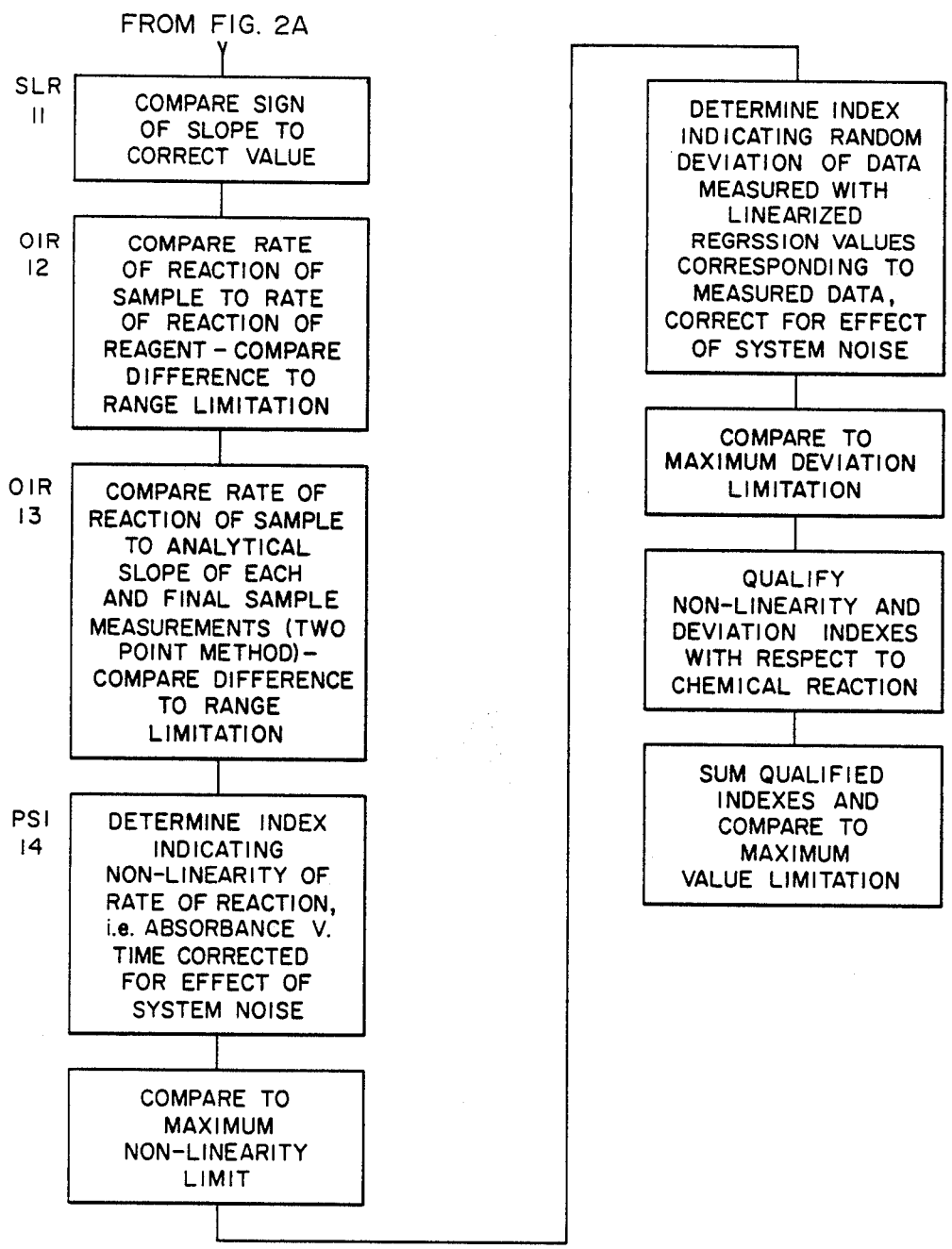

The presented method of validation is schematically illustrated in the block diagram of FIG. 2. With continued reference to FIG. 2 and with specific reference to graphical illustrations as indicated, the method will now be described.

The method of validation comprises three tiers of validation which may be used to judge the validity of the data received from the reaction rate measurement performed by the instrument. These tiers are illustrated generally on the block diagram in FIG. 2 by brackets I, II, and III which enclose the individual tests and steps included in each individual tier.

Finally, the initial absorbance value obtained from the electronics 40 may be compared with the absorbance value of the reagent alone to determine within empirical limitations that the sample introduced into the reaction vessel is suitable for analysis. Suitability means that a reactable sample has been introduced having qualitative and quantitative characteristics which permits the expected reaction to take place without interference so that accurate analysis of the catalyst (enzyme) may be performed.

A first tier of validation tests the ability of the detection and measurement device used in the analysis instrument to provide accurate data indicating the measured parameters of interest investigated during the course of the reaction. This tier is generally indicated by I in FIG. 2.

The first test performed in this tier of validation is calibration of the electronic measurement system. This test is performed by applying simulated signals of known voltages to the electronics 40, at a point in the circuit indicated as 80 in FIG. 1, and measuring the output signal which is applied to the ADC 52. The simulated input signal is generated by the simulated signal generator 63 which receives power from a power supply source (included) and applies the simulated signal to switch node 81. The switch 61 which transmits signals to the electronics 40 is controlled by a switch control 59. Switch control 59 is directed by the control computer 30 to complete a circuit with either the detector 39 or the simulated signal generator 63. When the first step of validation tier one is performed, the computer 30 instructs the switch control 59 to complete the circuit between the simulated signal generator 63 and the electronics 40. At all other times, the computer 30 instructs the switch control 59 to complete the circuit between the detector 39 and the electronics 40.

Upon instruction from the control computer 30, the simulated signal generator 63 provides known voltage signals which are applied to the electronics 40 at equally spaced time intervals. The voltage signals and the time intervals of their application are characteristics of those signals which the detector 39 generates in measuring the transmittance of light through a sample. Thus, with known signals applied to the electronics 40, predictable output signals will be generated by the electronics 40 which are measured and processed by the computer 30, and checked for linearity.

The simulated signals applied to the electronics 42 increase in voltage with a decade relationship. In other words, the simulated signals increase in magnitude, by powers of 10, as represented by a logarithmic curve, for each time interval. Thus, the logarithmic converter 42 and the electronics 40 should output a signal having equally incremented voltage. The output signal should exhibit an ideal linear relationship between the outputs responding to increases in signal voltage. Linearity of the voltage increases in the output signal with time must be maintained within a maximum deviation of plus or minus 5% of the mean signal voltage. However, it should be clear that more restrictive deviation limitations may be required to increase accuracy.

If the electronics 40 fails to show linearity within the selected range of deviation, the control computer 30 indicates an error message and prevents the instrument from performing further tests.

Following completion of the calibration of electronic measurement system, the switch control 59 is instructed by the control computer 30 to complete the circuit between the detector 39 and the electronics 40 and remove the simulated signal generator 63 from the circuit.

The next two tests of the first tier measure optical clarity of the reaction vessel. They require a measurement to be made of light transmittance through an empty reaction vessel 10, to determine absorbance of light by the vessel. Absorbance by the vessel 10 may indicate an incorrect reaction vessel is being used (e.g., highly absorbant material) or that the reaction vessel is not clean and hence contaminants are present which may interfere with the transmission of light through the vessel. This test may further indicate a defect in the light source 36 or its power supply 38.

The control computer instructs a reading to be made of light transmitted through the reaction vessel 10 by detector 39 which is applied to the electronics 40. The output received from port 56 of the electronics 40 is compared to a limitation value contained in memory 60 which is a maximum limit, indicating maximum absorbance permitted for the reaction vessel 10. If the signal received at port 56 is greater than the maximum value against which it is compared the test is considered invalid. If it is not, the computer 30 instructs the next test to be performed.

The reaction vessel absorbance measured in the first tier is a base absorbance usable in all subsequent tests and analyses. The value of this absorbance may be introduced into memory 60 for further computational use.

In the next step, the signal obtained from port 56 indicating light transmittance of the empty reaction vessel 10 is compared to all other signals representative of light transmittance of each of the other reaction vessels 10 in the instrument. The range of deviation in the transmittance signals measured for the total number of reaction vessels in the instrument is determined and compared to a maximum range of deviation permissible which is contained in the memory 60.

For instance, the signal of each reaction vessel 10 indicating light absorbance is compared with the signal most different for other reaction vessels. This comparison is performed for each reaction vessel, and the largest difference determined is identified as the range of deviation. If the range in deviation of the reaction vessels is greater than the maximum value held in memory 60, it can be expected that light absorbance of the reaction vessels themselves will interfere greatly with the analysis performed in reaction vessels. Thus, the analysis will be unable to accurately indicate reliable measurements of the rates of reactions performed in them. The range of deviation between highest absorbance and lowest absorbance for the total number of reaction vessels 10 in the instrument is preferred to be held to 0.1 absorbance units (A), however, the range of derivation may be reduced to increase accuracy. In this case, an error message is indicated and the instrument will be instructed by the computer 30 to cease operation.

The control computer 30 next instructs the reagent fluid system 16 to read the label on the reagent container 18 storing reagent for the analysis to be performed. The label and label reader for the reagent container 18 may be one of a number of systems known for providing information in digitized format. For example, the label on the reagent container may contain a bar code consisting of a number of spaced lines of varying widths and spacings, which can be read by a scanning infrared laser and laser detector, to receive information indicated by the bar code of the contents in the reagent container. Such information as chemical identification, quantity contained, and date of manufacture may be presented in this manner. The microprocessor 58 compares the information received from the label on the reagent container 18 with the information programmed in memory 60 characteristic of the analysis desired, to determine that: correct reagent is available to the reagent handling module 14 for introduction to the reaction vessel 10, that sufficient reagent remains to perform the desired number of analyses and that the reagent has not become too old to provide effective reaction with a sample. If any of these investigations indicate that the chemical reaction will not be performed correctly an error message is instructed to be given by the control computer 30 and instrument functions ceased. This completes the first tier of validation studies performed by the instrument.

As discussed, the limitation values used in determining proper function and indicating validity of tests performed are empirically determined in the manner desired.

The reagent contained in reagent container 18 is provided to the instrument only after having a number of validations performed on its quality and quantity. Rigid quality controls are applied to assure that the reagent possess the correct chemical composition without contaminants. Elements such as pH, purity, concentrations of constituents, cofactors, stabilizers, and others are all rigidly controlled so that validation of the reagent chemistry in the instrument is assumed unnecessary. However, under circumstances in which adequate controls are not applied to the reagent, validation of the reagent chemistry and purity, etc., would be an important step in this presented method of validating analysis results.

The second tier of validation in the presented method requires reagent to be introduced to the reaction vessel 10. This is accomplished as described previously by the reagent handling module 14 which is instructed by the control computer 30 to present a known quantity of reagent within the vessel.

The first test performed in tier two measures the absorbance of the reagent and the reaction vessel. This is performed by measuring transmittance of light through the reaction vessel containing the reagent and applying the signal obtained by the detector 39 to the electronics 40. The signal received from the electronics 40 at port 56 provides an indication of light absorbance.

The measurement of light absorbance of the reaction vessel alone (first tier) is subtracted from the measurement of light absorbance for the reaction vessel containing reagent. The resultant value is a measure of light absorbance of the chemical constituents of the reagent alone. This value is compared to a maximum limitation of absorbance permitted for the reagent which is held in memory 60. If the absorbance of the reagent is determined to be greater than the maximum limit, the test is indicated as invalid. Under these circumstances it can be assumed that a contaminating element or secondary reaction producing an interfering product is present in the reagent, which will interfere with the light transmission measurements which are used to determine an activity when the reagent is mixed with sample.

The maximum value of absorbance is determined empirically from performing a number of controlled tests, as previously described, using reagent mixtures which are clinically controlled with a very high degree of accuracy. These tests indicate a clear range of maximum values of absorbance permissible for reagent used in analyses of the type which are to be performed by the instrument.

A maximum absorbance value test for the reagent is particularly important for those analyses which require reagent to be mixed in the reaction vessel 10 by introduction of separate reagent components. This test may indicate that proper mixtures have been obtained, and that no contaminants have been introduced. Additionally, this test may be used to determine that the reagent chemistry has not deteriorated beyond a functional state and become unable to adequately support the enzymatic reaction to be studied.

The next test in the second tier of validation is performed by taking a ten point rate measurement of the reaction vessel and included reagent. The ten point rate measurement is performed as previously described, wherein a signal from detector 39 is received by the electronics 40 at ten equally spaced intervals determined by the control computer 30. These signals are then processed through the electronics 40 to provide an output signal at the port 56 which ideally should represent a linear expression of the increase in absorbance with time. After subtraction of the reaction vessel absorbance, a linear regression of absorbance on time is then calculated to determine the slope of absorbance versus time or reaction rate.

The slope, as discussed, is a measure of the rate of activity of any reaction which is producing a product or consuming a substrate having a responsive absorbance to the wavelength of light being passed through the reaction vessel. The output received from port 56 may thus have a linear regression calculation performed thereon to obtain a slope value for the reagent without sample.

The ten point rate test should be performed using only a frequency of light which is used in the kinetic reaction analysis, since only interference with measurement of that analysis is of concern in validation. Obviously, more than ten points may be taken to increase accuracy of the measurement.

The slope value determined from the measured data from the reagent along is compared to a range limitation. The range limitation is empirically determined from measurement of clinically prepared reagent as previously discussed. The limiting values of this range are specific to the particular reagent being analyzed and are contained in memory 60 for use by the microprocessor for each of the reagents adapted for use in the instrument.

The rate of reaction of the reagent without sample is known as the endogenous rate of reaction. This test will then determine that the reagent is suitable for performing accurate rate analysis of a sample. The test may clearly indicate if a secondary reaction is present in the reagent prior to introduction of the sample which will interfere with photometric analysis. It further yields a fingerprint of the reagent introduced into the reaction so that improper reactants may be clearly indicated.

The slope value calculated for the endogenous rate of reaction of the reagent may then be stored in memory for future use in subsequent validity tests where comparison with this activity measurement may be useful.

At this point of the validation method sample is added to the reaction vessel 10 in a precisely measured amount to initiate the kinetic (enzymatic) reaction in the vessel. Sample introduction is accomplished as described previously, by the sample handling module 22 which is instructed by the control computer 30 to introduce a known quantity of sample into the reagent within the reaction vessel. The unknown quantity of catalyst (enzyme) contained in the sample begins reaction of substrate contained in the reagent to produce a product which is known to absorb light energy of the frequency transmitted through reaction vessel for analysis. Thus, absorbance of light by any contaminant which may have been contained in the sample which will interfere with accurate analysis of the rate of product formation may be indicated. This can be determined because theoretical and empirical data known to represent the rates at which a reaction having an analyzed catalyst (enzyme) should begin, will permit determination of a time related value for comparison. Thus, if the absorbance of the sample solution at any selected time period is higher or lower than expected initial absorbance for the sample initially reacting with the known reagent, this difference can clearly indicate that a contaminant or side reaction has been introduced to the reaction through the sample. This would seriously reduce the ablity to measure the rate of product formation and invalidate the analysis of the rate of reaction.

Additionally, the initial absorbance signal obtained at port 56 of the electronics 40 from which reaction vessel absorbance has been subtracted, may be compared to a maximum value of instrument range, contained in memory 60. If the measured and calculated absorbance is greater than the maximum value contained in memory the test will be invalidated. The maximum value is determined by limitations of the measuring system including the detector and electronics so that measurements made in analyzing the rate of the kinetic (enzymatic) reaction will be known to not exceed the range of measurement of the measuring system at any point during the analysis. The maximum value is thus calculated from the specifications of the components of the electronics and the detector to assure that adequate range of accurate measurement is available with which to perform analysis.

A final step in the second tier comprises checking the temperature environment of the reaction vessel to determine whether or not the temperature at which the reaction is taking place is maintained at a selected value. The temperature must be maintained at 30° C. or 37° C. to obtain clinically significant results from the analysis. Thus, if it is found that the temperature is not maintained at one of these values, the test will be invalidated.

A third tier of validating data received from the detection and measurement system analyzing the rate of kinetic (enzymatic) reaction, presents a method for statistically assessing the reliability of the collective data. Prior to performing the third tier of validation, ten data points are taken at equal time intervals, to measure the activity of the reaction. The ten data points taken in measuring the activity are related to the time period at which they are taken to determine a rate of increase of their value with respect to time. This generally is referred to as the slope of a value versus time plot. The slope may be obtained, as discussed, by performing a least squares linear regression of the data on time to obtain an indication of the linear relationship which best fits the data obtained with respect to time. As in previous tiers, the absorbance value of the light energy absorbed by the reaction vessel is subtracted from each of the measured data points prior to the use in calculations.

The third tier comprises a first step in which a comparison is made between the value of each of the data points taken with a limitation value for the system, which is empirically determined and held in memory 60. This test is performed to assure that the values of data points measured do not exceed the maximum dynamic limits of the measurement system. The maximum limits of the system include the performance and range limitations of the detection and measurement systems. This limitation is identical to the system limitation for dynamic range used in tier 2.

The second step comprises determining the best fit linear relationship for the data measured, and comparing the slope of the relationship with an empirically determined maximum value. The linear relationship and experimental slope are determined by use of equations (1) and (2) using the least squares linear regression, previously described. The maximum value limitation is empirically determined by performance of a series of tests as also previously described.

If any of the values of the data points, or the value of the experimental slope, exceeds the respective maximum limit, an indication is present that the kinetic (enzymatic) reaction did not proceed as expected, or that unusually high concentrations of reactants or contaminants are present in the sample solution. In either case, the reaction is invalidated.

The same steps may be performed for decreasing rate kinetic reactions as are known to those in the chemical arts. This is accomplished by providing empirically determined minimum limits for data values and experimental slope, and performing the comparison as described. These values similarly can be determined from empirical investigation through performance of a series of tests.

This step investigates both the detection and measurement system, and the chemical system (i.e. reagent, etc.) to determine that they have functioned to obtain a valid reaction for analysis.

A third step comprises comparing the direction of change of the data values with respect to time, with the direction which is theoretically expected for the chemical reaction being studied. This is indicated by the sign (plus or minus value) of the experimental slope calculated in the previous step for the data values versus time. In other words, an investigation is made to determine whether the reaction is resulting in an increase or decrease in concentration of the measured reactant (normally the product). This test is performed to assure that there is no unusual or unexpected interference clearly evident in the kinetic reaction being measured, such as the reactive contaminant in the sample, insufficient reactive material in the sample, or the presence of an unexpected inhibitor or reaction denaturation. For increasing absorbance reactions, the slope sign must always be positive. Conversely, the decreasing absorbance reactions, the sign of the slope must be negative.

Figure 3:
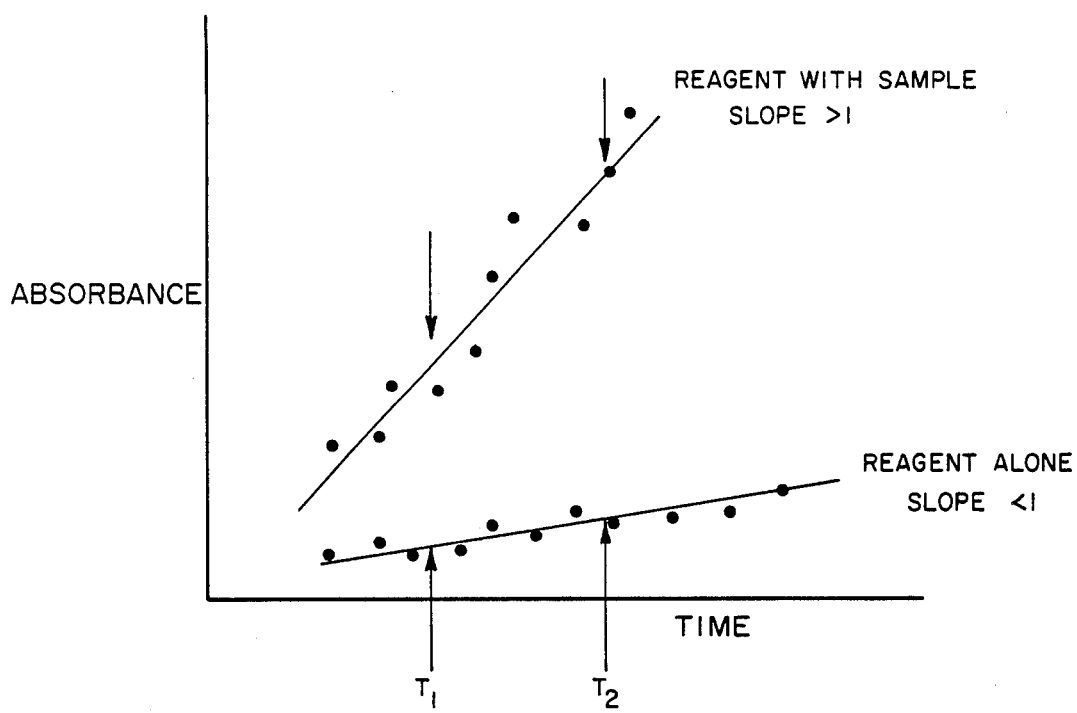
FIG. 3 is a graphical representation comparing an experimental rate of reaction with a rate of reaction obtained in the measurement of the endogenous activity of reagent alone (the second tier of validation).

The next fourth step comprises a comparison of the experimental rate of the reaction, i.e. the slope of absorbance versus time, with the rate of reaction obtained in the measurement of the endogenous reactivity of the reagent alone, which was done in the second tier. This test is particularly important for decreasing absorbance chemistries since the measured parameter of these chemistries is generally decreasing and thus has no maximum value which can be measured. The minimum values can become indeterminant in view of system noise and cannot be used for comparison with the system limit. The difference between the experimental and endogenous rates of reaction is compared to the maximum limitations expected for the chemical reaction, to determine whether a valid kinetic reaction has been obtained. The maximum limitations are determined empirically by the method described. The comparison of slopes for reagent with sample and reagent along is illustrated in FIG. 3.

The fifth step comprises comparison of the rate of reaction, i.e. slope of absorbance versus time, with a similar value calculated by using the initial data point following injection of sample into reagent, and the final data point obtained in measurement. The latter is termed a two point method or rate measurement, and is generally known. This method of determining rate of reaction or slope is described in the Clinical Enzyme Primer by George M. Sims, published by Beckman Instruments, Inc. in 1978. The initial data point should be the first available measurement obtained as soon as possible after initiation of the reaction. This is referred to as the two point value of the rate reaction, or two point slope.

Figure 4:
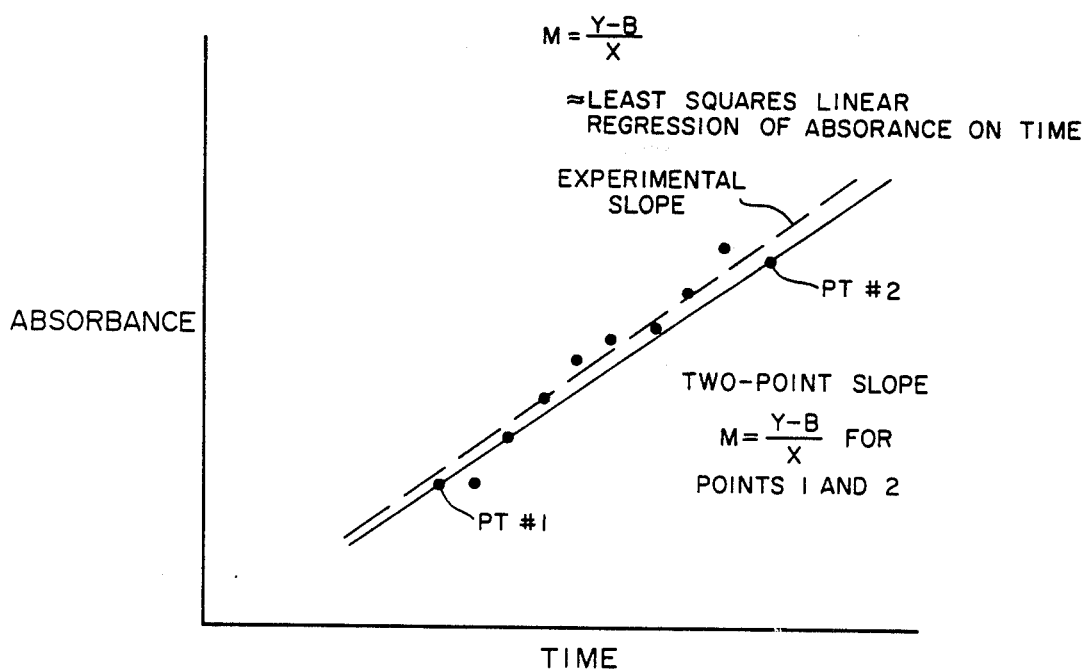
FIG. 4 is a graphical representation comparing experimental and two point slopes of measured data of the chemical reaction and determining a difference between them.

The experimental and two point slopes are compared and the difference compared to a range limitation which is empirically determined by the discussed method. This test is illustrated in FIG. 4, where the experimental linear relation and the two point linear relation can be seen. If the difference value of the slopes of these linear illustrations exceeds the range limitation, the test is considered invalidated.

The third tier comprises a sixth step in which an index is determined indicating nonlinearity in relationship between change (increase or decrease) in the data values measured and the passage of time. This generally indicates a nonuniform rate of reaction of a nonlinear slope, during the measurement period selected.

Figure 5:
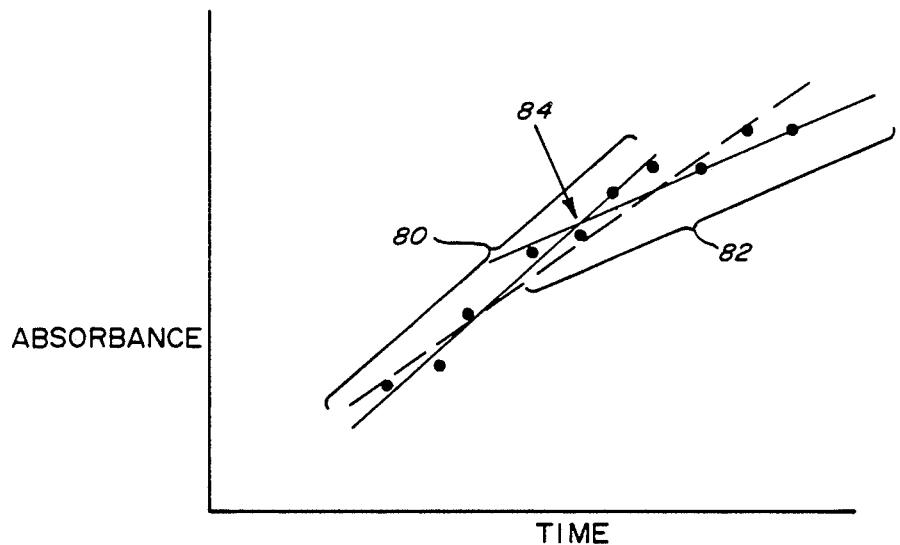
FIG. 5 is a graphical representation comparing rates of reaction for two individual segments of the data measured in analysis of the chemical reaction.

The sixth step is performed by comparing the rates of reaction, i.e. absorbance versus time, for at least two individual segments of the totality of data measured. Referring to FIG. 5, for instance, a rate of reaction versus time slope may be determined for a first selected group of data points, and this slope compared to the slope of a second selected group of data. Preferably, for a measurement consisting of ten data points, the first selected group 80 will comprise points 1 through 6 and the second selected group 82 will comprise points 5 through 10 so that there will be an overlapped range 84 between the groupings of data. This is preferred because more consistent and accurate determination of each slope segment is obtained by this method due to increased numbers of data points in each segment. The overlapping portions also tend to decrease arbitrary slope calculations. The difference in the rates of reaction or slopes of the two individual segments is then determined and compared to a maximum allowable difference which is determined empirically by performance of a multitude of clinically controlled tests, as discussed.

The nonlinearity index may be determined through use of the following formula:

$$\text{Nonlinearity Index} = \frac{WF * |PS_1 - PS_2|}{\sqrt{\left|\frac{PS_1 + PS_2}{2}\right|} + LF}$$

where:
$PS_1$ is the slope equals the slope of the first segment,
$PS_2$ equals the slope of the second segments,
WF equals the weighting factor, and
LF equals the linearizing factor.

A seventh step comprises the determination of an index indicating the magnitude of random noise or deviation evident in the data obtained from which the rate of reaction will be determined. The seventh test is performed by obtaining a measure of the relative scatter of the measured data points. This may be determined by summing the difference between the measured value of each data point and the best fit value indicated by the best fit linear relationship. The best fit value is determined by performing a least squares linear regression on the data obtained to determine the linear relationship best fitting the data. This is the same calculation as has been discussed to determine the experimental slope. The linear relationship obtained from the regression will indicate a best fit value for each time at which a data point was obtained. The best fit value can then be compared to the actual measured value to determine a difference in value. These differences between measured and linearized data points are then added to obtain an indication of the total scatter of the measured data from the linearized estimation of such data.

Figure 6:
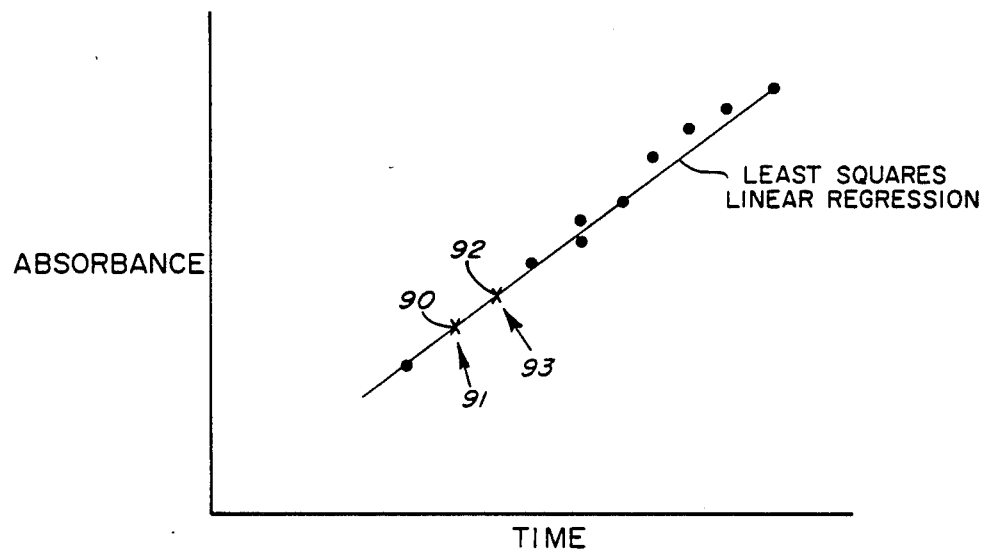
FIG. 6 is a graphical representation of determining a best fit linear relationship for data collected relating to the kinetic reaction.

This test can be visualized with reference to FIG. 6 in which a set of data is plotted on a graph of absorbance versus time. The best fit linear relationship is indicated as the least squares linear regression which is a line that most accurately fits through the collective data points. Each measured data point may then be compared to a corresponding point on the line for the same time period. The differences between each set of points may then be determined and summed to give an indication of total point scatter. For instance, measured point 91 may be compared to linearized point 90 to determine the difference in their absorbance values. Similarly, measured point 93 may be compared with linearized point 92 to obtain a difference in absorbance value. After such difference is determined for each point, the differences may be summed to obtain an indication of point scatter in the best fit linear relationship.

The deviation index may be determined through use of the following formula:

$$\text{Deviation Index} = \frac{WF * \Sigma |A_i - A_i|}{|Slp| + LF}$$

where:
$A_i$ equals an observed or measured absorbance,
$A_i$ equals the calculated or best it absorbance value,
Slp equals the slope of the best fit linear relationship,
WF equals the weighting factor, and
LF equals a linearizing factor.

The indexes determined in the sixth and seventh steps of the third tier are combined for comparison with an empirically determined total index which is specific to the chemical reaction being examined. These tests are used to determine whether or not the data received is sufficiently accurate and reliable for clinical use. Each of the indexes determined are corrected through the determination to take into account the actual effect of noise in the detection measurement and chemical systems. The noise affecting accuracy or reliability of measurement of the reaction rate, includes any and all non-reaction factors that can cause the ten data ratings obtained to deviate from their theoretical linear relationship with time. From a clinical significance standpoint, the source of noise introduction is unimportant. Rather, the fact that excessive noise is entered into the measurement of the reaction is sufficient to determine invalidity of the measurement as far as clinical significance is concerned.

The error indexes determined in each of the sixth and seventh steps are corrected to reflect the significance which system noise introduces into the reliability of the absorbance measurements, and thus the rate of reaction measurement. For instance, for data values which are large in magnitude compared to the level of noise in the system, or for data values whch rapidly increase with respect to time to result in a large magnitude value when compared with the level of noise, the magnitude of noise level which is acceptable without affecting clinical significance of the result is much greater.

Figure 7:
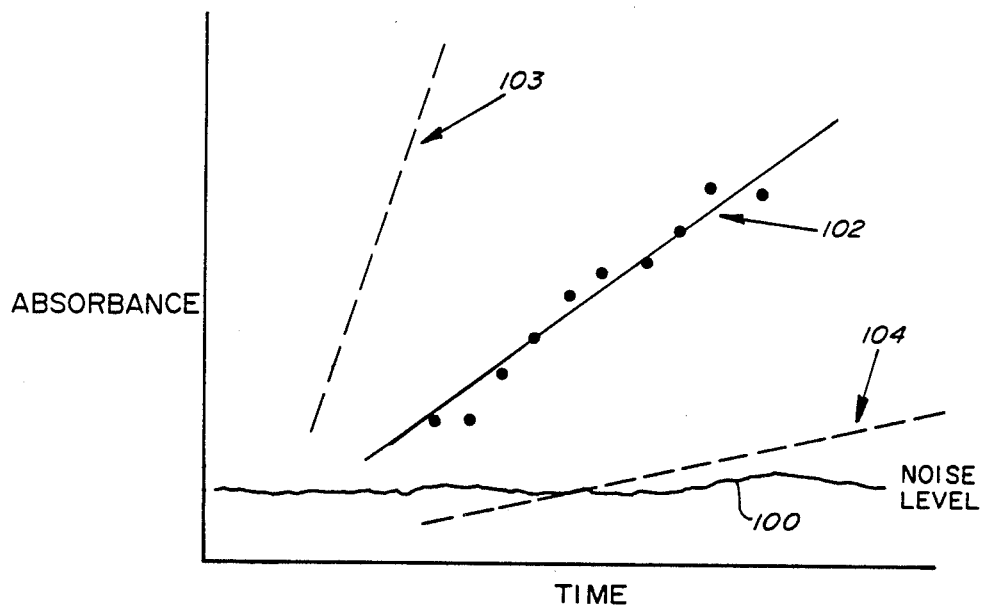
FIG. 7 is a graphical illustration indicating the effect on reliability of noise in a measurement system for the chemical reaction.
Figure 8:
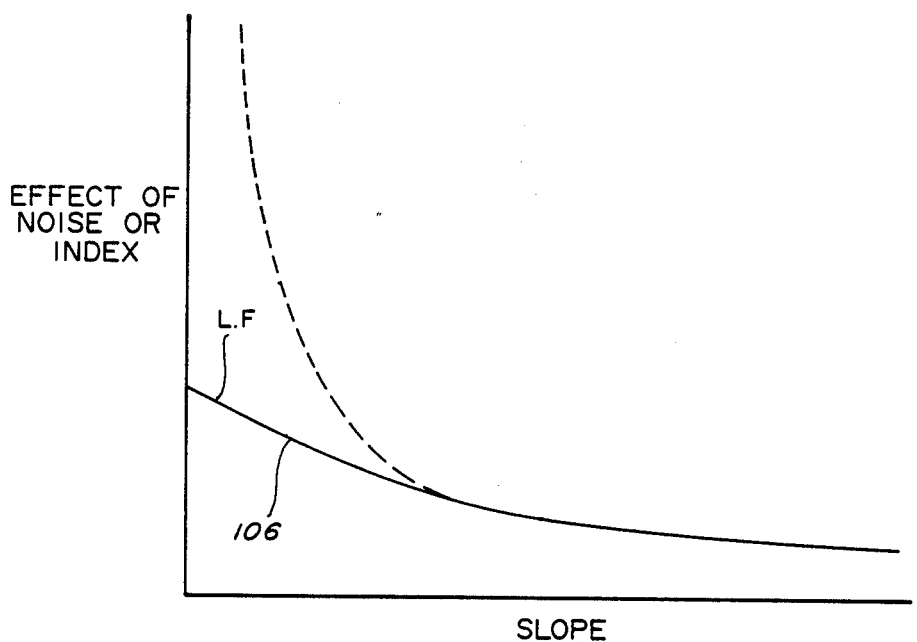

However, where the magnitude of the data values obtained is small, or the rate of change of these values with respect to time is small, even a moderate noise level may seriously affect reliability in the data obtained. This is illustrated in FIG. 7 where the noise level of the system is indicated by the line 100. For a normal magnitude data set, indicated as 102, the level of noise illustrated would have little significance on the values of the data obtained. At the very most (early points), noise comprises approximately 50% of the measured value. However, very quickly the magnitude of the value of data points increases to substantially reduce the percentage of noise comprising part of the measurement.

A similar characteristic is true for a data group indicated as 103 for a very rapid rate of reaction in which the data values quickly increase to substantially reduce the effect of noise in their measurement. However, for the data group represented as 104, the noise level is significant throughout the measurement of data points and in fact is very possibly greater than the measurable value of the data point at early time periods.

Thus, it can be seen that the effect of noise must be given greater weight for data groups such as 104, while it may be given lesser concern for data groups such as indicated by 103. The total noise level permissible in obtaining a clinically significant result is much greater for a data group such as 103, than would be the case for the data group 104. Where the data group such as 104 clearly exhibits integrity in the linear relationship between the values measured, the noise may again be permitted a larger involvement while maintaining clinically significant results.

Correction for these noise factors is applied to each of the indexes obtained in steps 6 and 7 to take into account the effective noise on the data obtained. This is accomplished in the sixth test by dividing the difference in slopes calculated by the square root of their average. In the seventh step, the summation of deviations is divided by the absolute value of the slope of the best fit linear relation. Thus, in both of these index determinations, increased rates of reaction, which result in increased slope values, causes reduced sensitivity to external factors such as noise due to the larger value expressed in the denominator of each index relationship. This sensitivity adjustment generally permits a larger magnitude noise limit for larger magnitude data values, and conversely lower magnitude noise limits for smaller magnitude data values. Additionally, the sensitivity adjustment may permit noise measurement to comprise a larger percentage of a lower value data group if it is clear that the data measured expresses a reliable result, whereas a lower percentage of noise is permissible in higher value data groups.

Each of the index calculations includes a linearizing factor LF. The effect of the linearizing factor can be described with reference to FIG. 7. As can be seen from the plot of noise effect versus the slope, as the slope or rate of reaction becomes very small, each of the index calculations tends to become very large approaching infinity. This is due to the fact that a slope related parameter is included in the denominator of each calculation. Thus as the slope becomes very small, the denominator tends to go to zero which results in an infinite value for the index being determined. Thus, a linearizing factor has been added to the determination of each index which effectively limits the magnitude of the index as the slope or rate of reaction determined by a given data set becomes small. The linearizing factor is selected empirically by performing a test series as described, and is specific to the particular chemical reaction being performed. The linearizing factor being a constant tends to stabilize the index value at small rates of reaction, i.e. small slopes as indicated in the Figure by line 106.

A weighting factor is applied to each of the indexes calculated to correct the index for the particular chemistry being investigated. Each of the weighting factors is determined empirically by performing a series of tests as described previously, and are stored into the memory 60 of the control computer 30 for application to these tests.

The indexes determined in tests 6 and 7 are summed and compared to a standard value. If their total is larger than the value, the test is considered invalid. Thus, a data set may exhibit greater nonlinearity when data point deviation is small. Conversely, a data set may exhibit less nonlinearity when data point deviation is large. In combination, significant values for both indexes indicating moderate levels of nonlinearity and deviation may be sufficient to invalidate the test.

Generally, the standard index is selected at a value of 100 and each of the indexes is selected by application of the weighting factor to equal a combined value for a specific chemistry of between 20 and 25 when empirically determined to performance of clinically controlled tests.

What is claimed is:

1. A method for validating measurements made of a sample undergoing a kinetic chemical reaction for use in a scientific instrument including a system for measuring and a system for processing measured information of a sample material undergoing a kinetic chemical reaction comprising:

a first step of validating the ability of the measurement system being used in said instrument to measure the chemical reaction to provide accurate measurement of a significant parameter of the chemical reaction, before initiation of the chemical reaction;

initiating a kinetic chemical reaction with the sample material;

a second stop of validating the initiation of the chemical reaction and progress of the chemical reaction in a controlled manner;

measuring the kinetic reaction with said sample material and obtaining data relating to said measurement;

a third step of validating the data measured indicating information regarding said significant parameter in the chemical reaction, said third step comprising:

first determining that values of data obtained from measurement of the reaction do not exceed the ability of the measurement system to perform said measurements;

second, determining that values of data obtained from measurement of the reaction are within a selected range of deviation from the theoretically expected measurements of the reaction; and third, determining that random deviation of measurements of the reaction from theoretically expected measurements are within a selected range of deviation; and providing validated data to the system for processing measured information of a sample material undergoing a kinetic chemical reaction.

2. A method for validating measurements made of a sample undergoing a kinetic chemical reaction for use in a scientific instrument including a system for measuring and a system for processing measured information of a sample material undergoing a kinetic chemical reaction comprising:

a first step of validating the ability of the measurement system being used in said instrument to measure the chemical reaction to provide accurate measurement of a significant parameter of the chemical reaction, before initiation of the reaction;

initiating a kinetic chemical reaction with the sample material;

a second step of validating the initiation of the chemical reaction and progress of the chemical reaction in a controlled manner;

measuring the kinetic reaction with said sample material and obtaining data relating to said measurement;

a third step of validating the data measured indicating information regarding a significant parameter in the chemical reaction, said third step comprising:

first determining that values of data obtained from measurement of the reaction do not exceed the ability of the measurement system to perform said measurements;

second, determining a sum of deviations of individual data points measured from a least squares linear regression of all data points measured, and dividing said sum by the slope of said linear regression, to determine an index of random deviation;

third, determining a partial slope of at least two segments of the data measured, each segment comprising a group of data points, less than the whole of said data, determining a difference between the partial slopes of said segments and dividing each determined difference in slope by a square root of an average value of the partial slopes to determine a non-linearity index indicating a non-linear relationship of said date; and fourth, comparing a sum of said indexes with a selected value limitation characteristic of the specific chemical reaction being measured; and providing validated data to the system for processing measured information of a sample material undergoing a kinetic chemical reaction.

* * * * *